United States Patent
Smolik et al.

[19]

[11] Patent Number: 5,662,991
[45] Date of Patent: Sep. 2, 1997

[54] LAMINATED BIOCIDAL FABRIC

[75] Inventors: Tayyibe Smolik, Gefrees, Germany; Mark E. Carr, Clarks Summit; Robert A. Sallavanti, Dalton, both of Pa.

[73] Assignee: Gentex Corporation, Carbondale, Pa.

[21] Appl. No.: 363,700

[22] Filed: Dec. 23, 1994

[51] Int. Cl.$^6$ .............................. A61L 15/16; A61K 9/70; A61F 13/00
[52] U.S. Cl. .................... 442/319; 424/449; 424/402; 424/404; 424/411; 424/447; 424/448
[58] Field of Search .................. 424/449, 402, 424/404, 411, 447, 448; 428/246, 288, 289

[56] References Cited

U.S. PATENT DOCUMENTS

| | | | |
|---|---|---|---|
| 4,615,937 | 10/1986 | Bouchette | 428/289 X |
| 5,085,653 | 2/1992 | Levy | 604/358 |
| 5,143,582 | 9/1992 | Arkens et al. | 428/285 X |
| 5,273,757 | 12/1993 | Jaeger et al. | 424/449 X |
| 5,328,696 | 7/1994 | Noel | 424/449 |
| 5,350,625 | 9/1994 | Peterson et al. | 428/299 X |
| 5,374,429 | 12/1994 | Kinoshita et al. | 424/449 X |
| 5,417,974 | 5/1995 | Sekiyama et al. | 428/411.1 X |
| 5,433,987 | 7/1995 | Peterson et al. | 428/299 X |

*Primary Examiner*—Daniel Zirker
*Attorney, Agent, or Firm*—Shenier & O'Connor

[57] ABSTRACT

A biocidal fabric in which a pattern of clusters of biocidal beads are adhered between an air pervious substrate and a cover which may be gas impervious, water-vapor pervious or gas pervious. In the method and appratus for making the fabric, a pattern of hot melt adhesive is applied to the substrate and beads of biocidal material are sprinkled over the adhesive, after which the excess beads are removed. The same pattern of adhesive is applied to the cover and the cover adhesive is brought into contact with the beads on the substrate to complete the fabric.

14 Claims, 4 Drawing Sheets

FIG. 3
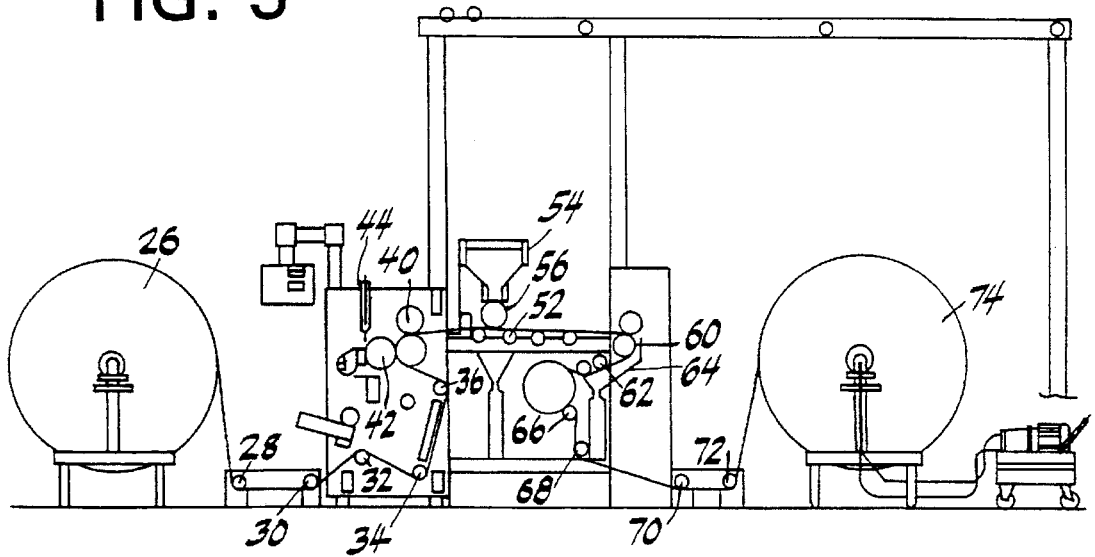
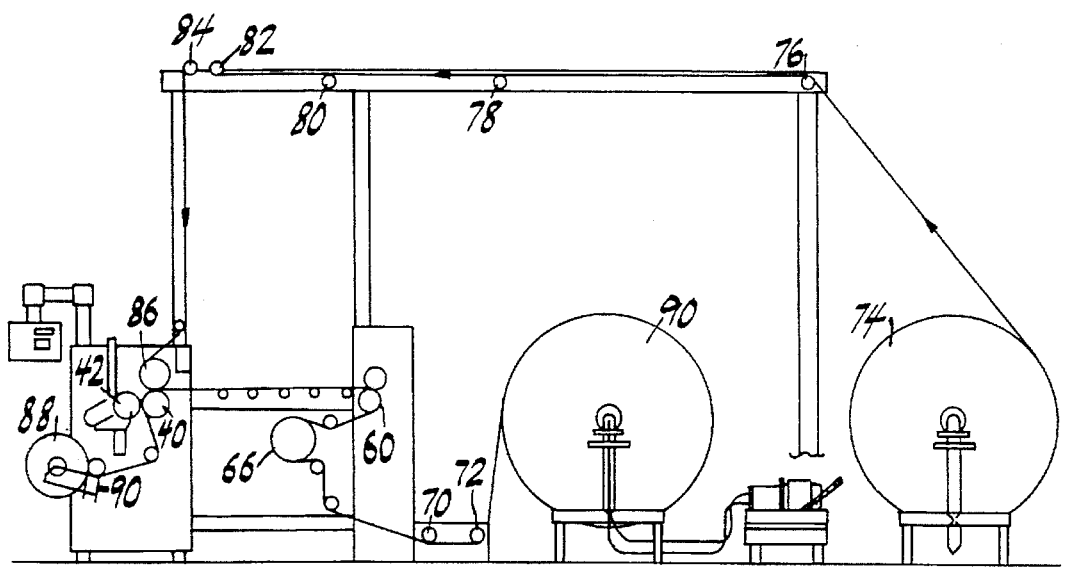
FIG. 4

5,662,991

LAMINATED BIOCIDAL FABRIC

FIELD OF THE INVENTION

The invention is in the field of biocidal materials and, more particularly, relates to a laminated biocidal fabric of general use.

BACKGROUND OF THE INVENTION

There are known in the prior art various biocidal materials. Various attempts have been made in the prior art to incorporate these materials in medical devices, such as sponges, gloves, pads and the like. Other attempts have been made in the prior art to incorporate biocidal materials in substrates which can be formed into medical appliances.

While the efforts in the prior art to form biocidal material which is capable of being formed into medical devices have been more or less successful, they have not resulted in production of a biocidal fabric which is versatile as is desired.

SUMMARY OF THE INVENTION

One object of our invention is to provide an improved biocidal fabric.

Another object of our invention is to provide a biocidal fabric which is useful as a general industrial cloth in the biomedical food and pharmaceutical industries.

A further object of our invention is to provide a method of making an improved biocidal fabric.

A still further object of our invention is to provide apparatus for making an improved biocidal fabric.

Another object of our invention is to provide a biocidal fabric which is useful in the protection of workers in biohazardous zones.

Yet another object of our invention is to provide a biocidal fabric which is useful in the contamination control of biosensitive products.

Other and further objects of our invention will appear from the following description.

BRIEF DESCRIPTION OF THE DRAWINGS

In the accompanying drawings to which reference is made in the instant specification and which are to be read in conjunction therewith and in which like reference numerals are used to indicate like parts in the various views:

FIG. 3 is a side elevation of the apparatus employed in making our laminated biocidal fabric in the initial stage of the process.

FIG. 4 is a side elevation of the apparatus illustrated in FIG. 2 showing the final stages in the process of making our laminated biocidal fabric.

DESCRIPTION OF THE PREFERRED EMBODIMENT

Figure 1:
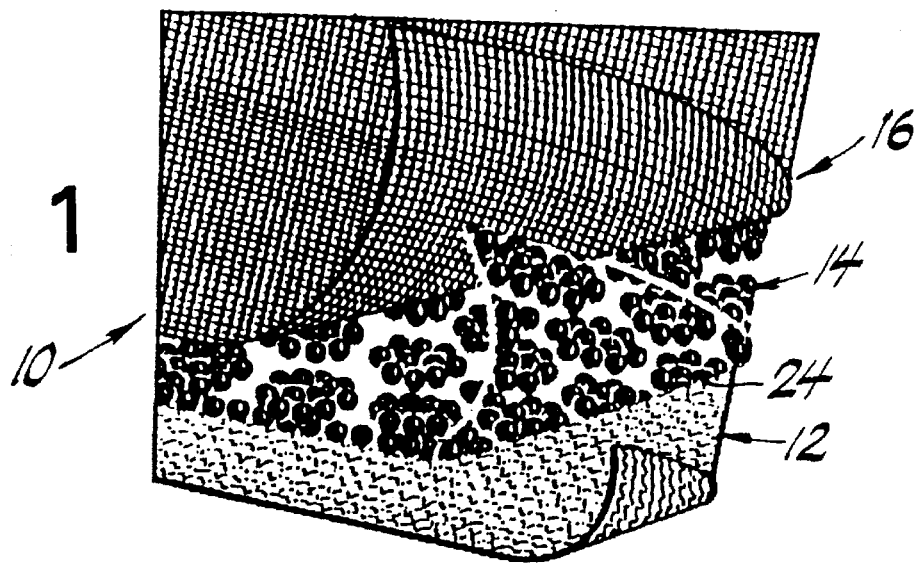
FIG. 1 is a perspective view of our laminated biocidal fabric with the layers separated more clearly to illustrate the nature of the fabric.
Figure 2:
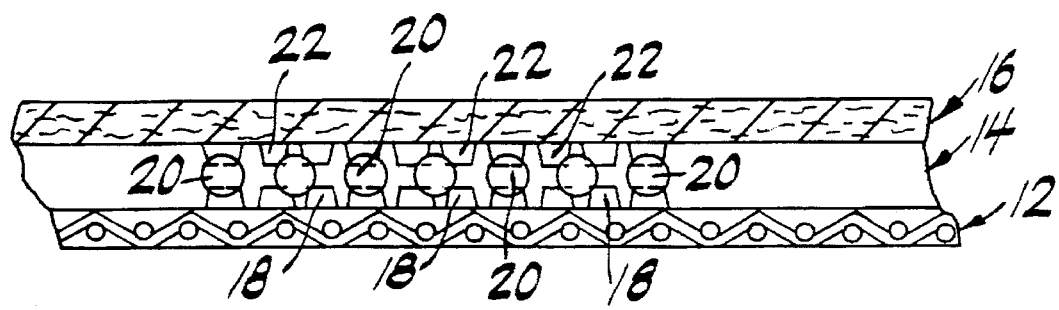
FIG. 2 is a sectional view of the fabric illustrated in FIG. 1 drawn on an enlarged scale.
Figure 7:
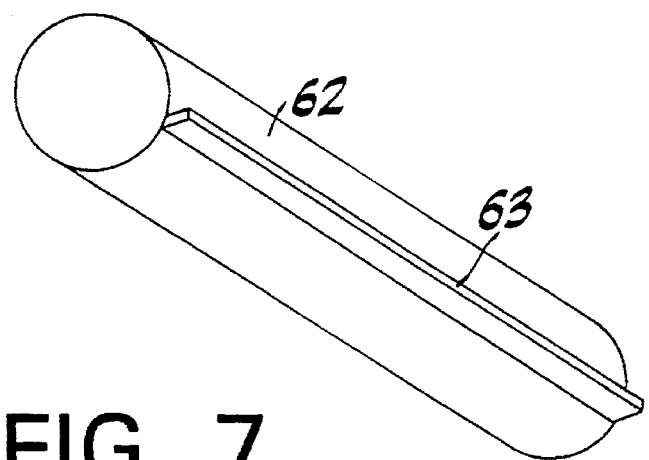
FIG. 7 is a perspective view of the fabric agitating device of the apparatus illustrated in FIGS. 2 and 3.
Figure 5:
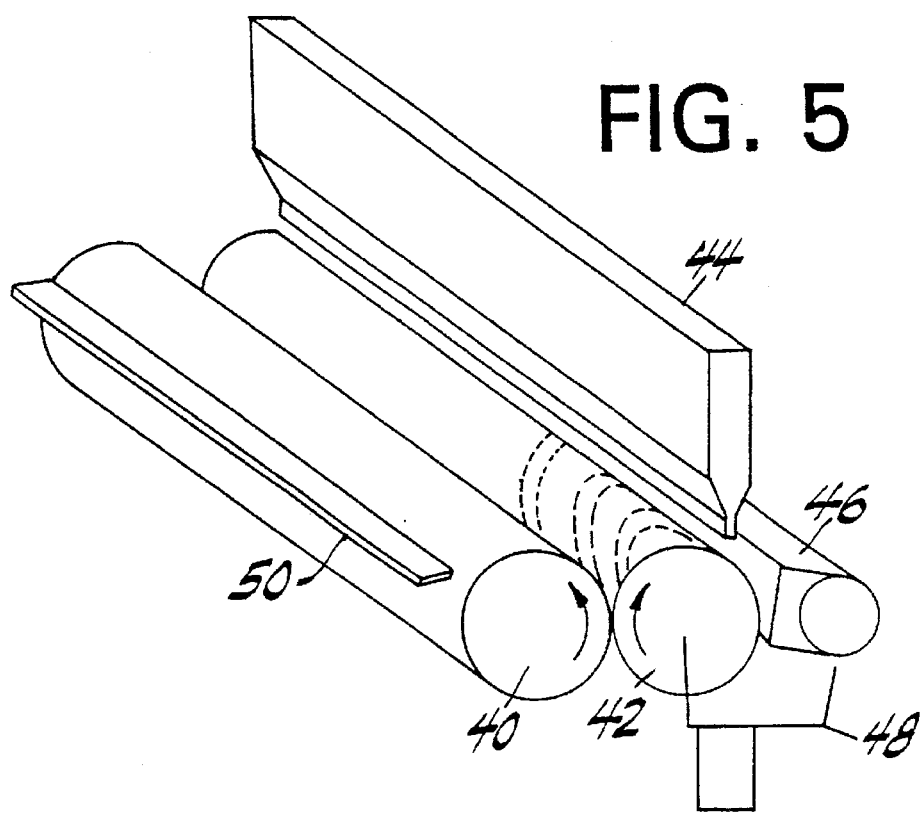
FIG. 5 is a perspective view of the hot melt adhesive applying system of the apparatus shown in FIGS. 2 and 3.
Figure 6:
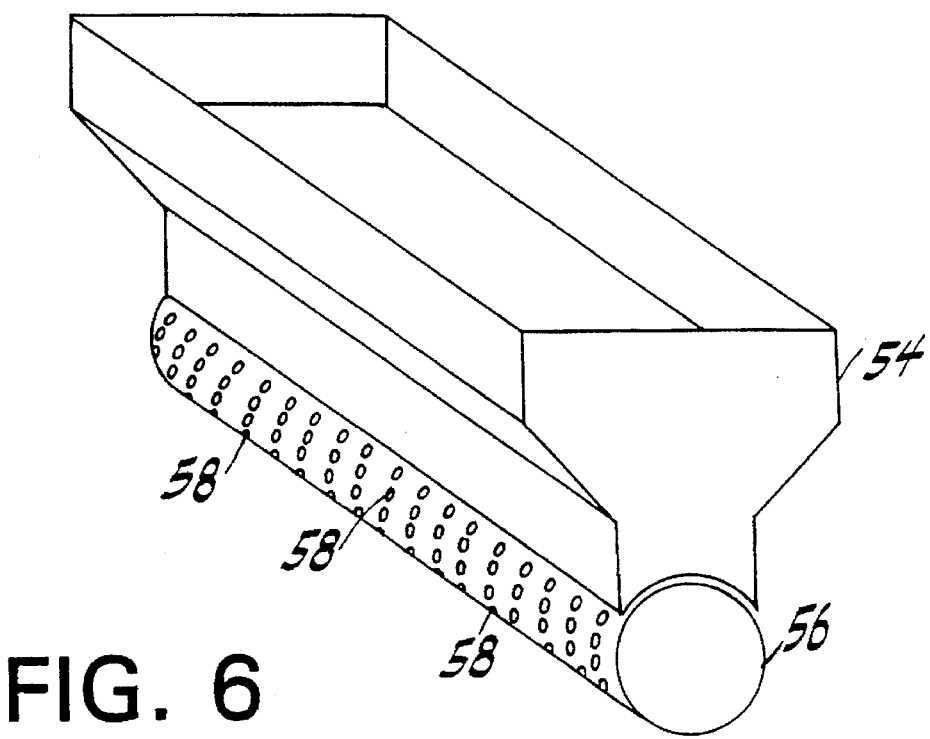
FIG. 6 is a perspective view illustrating the details of the bead applying device of the apparatus shown in FIGS. 2 and 3.

Referring now to FIGS. 1 and 2, our laminated biocidal fabric indicated generally by the reference character 10 includes a substrate 12 which may, for example, be a polyester tricot knit. The fabric 10 includes an intermediate layer 14 containing biocidal material to be described more fully hereinbelow. A cover fabric which may for example be a melt blown coaxial polyamide/polyester non-woven fabric completes the assembly 10.

Figure 8:
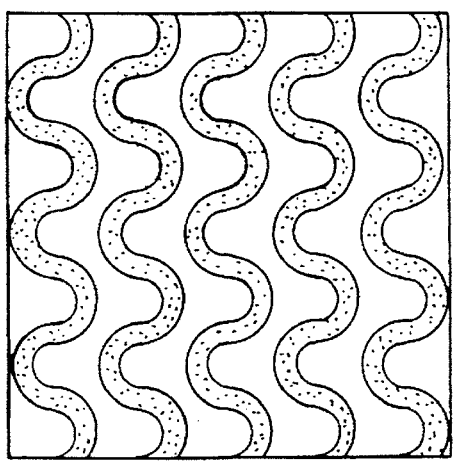
FIG. 8 is a plan view of one pattern of hot melt adhesive we may employ in our laminated biocidal fabric.
Figure 9:
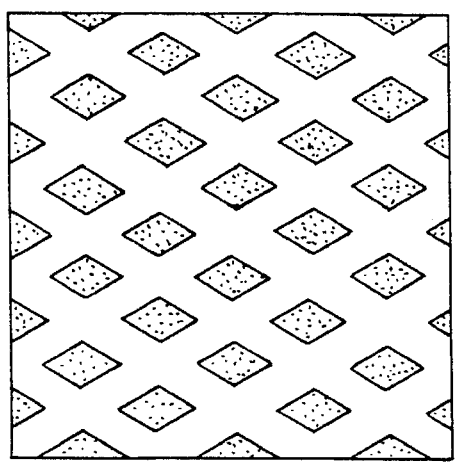
FIG. 9 is a plan view of an alternate form of adhesive pattern which we may employ in our laminated biocidal fabric.
Figure 10:
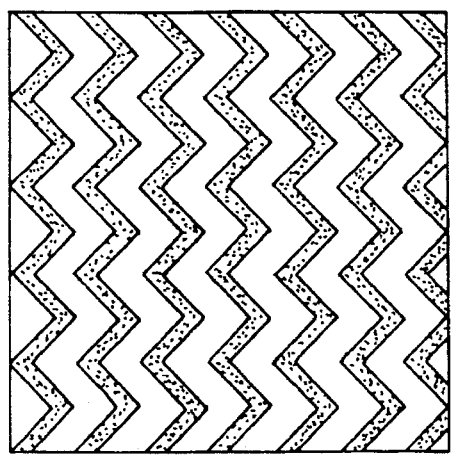
FIG. 10 is a plan view of a further form of adhesive pattern we may employ in our biocidal fabric.
Figure 11:
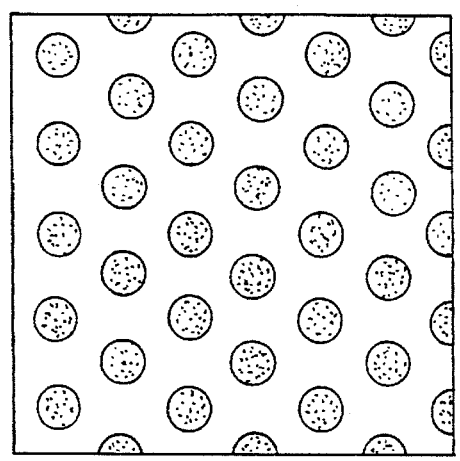
FIG. 11 is a plan view of yet another form of adhesive pattern which we may employ in our laminated biocidal fabric.

As can best be seen by reference to FIG. 2, the intermediate layer 14 includes a plurality of dots 18 of hot melt adhesive which may for example be a reactive polyurethane hot melt adhesive applied to the surface of substrate 12 in a predetermined pattern of dots 18. For example, the dots 18 may form a sinusoidal pattern as illustrated in FIG. 8. Alternatively, they may be diamond shaped groups of dots 18 as shown in FIG. 9. Still further, the group of dots 18 may form zig-zag patterns as illustrated in FIG. 10 or may form circles, each of which includes a group of dots 18 as illustrated in FIG. 11.

As will be described more fully hereinbelow, we apply a plurality of biocidal beads 20 to the adhesive 18. After applying the beads 20, we apply a pattern of dots 22 of the hot melt adhesive to the cover fabric 16 and then bring the adhesive on the cover fabric 16 into contact with the beads 20 of the intermediate layer 14. The result is the fabric shown in FIG. 1 in which the intermediate layer 14 includes a plurality of clusters 24 of biocidal beads 20. It will be appreciated that care should be taken that the pattern of adhesive on the cover layer 16 registers with the pattern of beads on the substrate 12.

As the biocidal material of our laminated biocidal fabric, we employ biocidal resin beads of the type described in International Application Ser. No. PCT/CA93/00378 filed 15 Sep. 1993 (Publication WO94/06296). For certain applications both the substrate 12 and the cover fabric 16 are air permeable. For medical applications such as protective clothing or bandages, we may use a gas-tight film for the cover 16. Such a structure would be suitable where sterile conditions are to be maintained inside a bandage, for example. Alternatively, the cover 16 may be of water-vapor permeable material such as GORE-TEX, which is the registered trademark of W. L. Gore & Associates, Inc. of Newark, Del. for such fabrics. In all cases substrate 12, which is layer next to the skin, is gas-permeable. In order to preserve the air permeability of the laminated fabric assembly and to maximize the effect of the biocidal beads, typically we cover only 30 to 32% of the area of the substrate with adhesive. While we could cover as much as 80% of the area, at that point you begin to lose control of the adhesive and the areas of adhesive start to merge in such a way as deleteriously to affect the permeability of at least the substrate 12 of the overall fabric.

More specifically, the beads we employ are formed of a resin which is a polypropylene polymer along whose molecular chain links are quaternary ammonium ion moeites, the charge of which is counterbalanced by polyiodide ions in immediate proximity. When cellular entities such as bacteria, viruses, fungii, cellular cysts, cellular bodies/body fluid components (red blood cells, platelets, etc.) encounter this resin, they are preferentially attracted to the charged ion sites on the polymer matrix. Once binding to these sites, a reduction-oxidation reaction occurs whereby molecular iodine is emitted in unit surges. The emitted iodine attacks the cellular membrane, oxidizes it to cellular fragments (kills the cell), and becomes harmless iodide ions as a result.

While we prefer to use hot melt adhesives, the beads 20 are thermoplastic so that you cannot apply them in a high heat environment. In our apparatus, to be described hereinbelow, the substrate to which the hot melted adhesive is applied moves through the apparatus at about two meters per minute. It could move through at a speed in the range of two to ten meters per minute. In any event, by the time the beads are applied, which is about thirty seconds after the application of the adhesive, the adhesive is tacky and not so hot as would melt the beads.

One form of our fabric 10 is of the order of one to two millimeters thick, air permeable at ambient non-forced flow rates of the order of meters per hour and it retains flexibility for ease of use in garments, face shields, bandages, blankets and the like, while maximizing the biocidal capacity of the beads 20.

Referring now to FIGS. 3 to 7, in the apparatus on which we practice our method of forming a laminated biocidal fabric, a roll 26 of the substrate 12 is supported on a stand and fed past guide rollers 28, 30, 32, 34, 36 and 38 to the nip between a backing roll 40 and an embossed patterning roll 42. As can best be seen by reference to FIG. 5, the embossed patterned roll 42 has a surface provided with a plurality of dots arranged in a pattern or in groups corresponding to the pattern of adhesive to be applied to the substrate 12. An adhesive supply 44 feeds hot melt adhesive to the roll 42 which is heated by a heater 44. The roll 42 rotates in a direction to apply the adhesive to the surface of fabric 12 in the predetermined pattern. A blade 50 associated with the roller 40 is adapted to remove excess adhesive from the roll.

After leaving the nip between the rolls 40 and 42, the substrate passes over a train of rollers 52 and below a hopper 54 adapted to contain a supply of the biocidal beads 20. As can best be seen by reference to FIG. 6, a distributor roller 56 associated with the hopper 54 is provided with a plurality of pockets 58 so that the beads are evenly distributed across the surface of the substrate 12.

After leaving the bead applying station, the substrate 12 is inverted by an inverting roller 60 and passes by an agitator roller 62 provided with a blade 63 which, as the roll 62 rotates, beats against the substrate 12 to cause excess beads in the area of the substrate surface not provided with adhesive to fall off the substrate to be collected in a trough 54 forming part of a vacuum system for collecting the excess beads and returning them to the hopper 54.

The substrate 12 travels from the agitator 62 to bring the bead carrying surface thereof into proximity with a cooling roll 66 which causes the heat melted adhesive to set. After the adhesive has set, the substrate travels around guide rollers 68, 70 and 72 to a windup roll 74 which forms a roll of the substrate bead side out.

After the biocidal beads have been applied to the surface of the substrate 12, in order to complete the fabric the roll 74 is positioned adjacent the apparatus and the substrate 12 is trained around guide rollers 76, 78, 80, 82 and 84 and is directed to the nip between a pressure roll 86 and the backing roll 40. At the same time a roll 88 of the cover fabric is placed on an unwind stand 90 and is directed to the nip between the applicator roller 42 and the backing roller 40. In this way, a pattern of adhesive dots similar to that which was applied to the substrate 12 is applied to the cover 16. After the adhesive have been applied to the cover in the manner described, the cover fabric is passed into the nip between rollers 86 and 40 to bring the adhesive pattern on the cover into engagement with the clusters of beads on the surface of the substrate 12. When that has been done, the cover fabric is adhered to the beads and the assembly of the substrate 12, the beads and the cover 16 is passed around roller 60 and around cooling roller 66 and past guide rollers 70 and 72 to a roll 90 driven by a suitable takeup to form a coil of the finished product. As has been pointed out hereinabove, care should be taken that the pattern of adhesive on the cover 16 registers with the pattern of beads as the cover is brought into proximity with the beads.

It will be seen that we have accomplished the objects of our invention. We have provided a biocidal fabric which is useful as a general industrial cloth in the biomedical food and pharmaceutical industries. Our biocidal fabric is useful in the protection of workers in biohazardous zones and in the continuation control of biosensitive products. We have provided a method of and apparatus for making our biocidal fabric.

It will be understood that certain features and subcombinations are of utility and may be employed without reference to other features and subcombinations. This is contemplated by and is within the scope of our claims. It is further obvious that various changes may be made in details within the scope of our claims without departing from the spirit of our invention. It is therefore to be understood that our invention is not to be limited to the specific details shown and described.

Having thus described our intention, what we claim is:

1. A biocidal fabric including in combination
  a gas-permeable lower layer of material,
  a single intermediate layer comprising a plurality of spaced biocidal beads,
  an upper layer of material,
  first means for adhering the beads to the lower layer, and
  second means for adhering the beads to the upper layer,
  wherein both adhering means comprise an adhesive.

2. A biocidal fabric as in claim 1, wherein the beads and the adhering means are formed in patterns which register with one another in a direction normal to the layers.

3. A biocidal fabric as in claim 1, wherein the beads are adhered to the layers in spaced clusters.

4. A biocidal fabric as in claim 1, wherein portions of the lower layer are free from adhesive to preserve the gas permeability of the lower layer.

5. A biocidal fabric as in claim 1, wherein the beads emit iodine upon contact with cellular entities.

6. A biocidal fabric as in claim 1, wherein said upper layer is gas-impermeable.

7. A biocidal fabric as in claim 1, wherein said upper layer is water-vapor permeable.

8. A biocidal fabric as in claim 1, wherein said upper layer is gas-permeable.

9. A biocidal fabric as in claim 1, wherein said lower layer is a knit fabric.

10. A biocidal fabric as in claim 1, wherein said lower layer is a polyester.

11. A biocidal fabric as in claim 1, wherein said upper layer is a nonwoven fabric.

12. A biocidal fabric as in claim 1, wherein said upper layer is a meltblown, nonwoven fabric.

13. A biocidal fabric as in claim 1, wherein said upper layer is a meltblown polyimide/polyester nonwoven fabric.

14. A biocidal fabric as in claim 1, wherein both adhering means comprise a hot melt adhesive.

* * * * *